(12) United States Patent
Hoffman et al.

(10) Patent No.: US 9,028,805 B2
(45) Date of Patent: May 12, 2015

(54) CONDITIONING COMPOSITION FOR HAIR

(75) Inventors: Martin Hoffman, Zwingenburg (DE); Michael Molenda, Frankfurt (DE)

(73) Assignee: Kao Germany GmbH, Darmstadt (DE)

( * ) Notice: Subject to any disclaimer, the term of this patent is extended or adjusted under 35 U.S.C. 154(b) by 0 days.

(21) Appl. No.: 13/513,718

(22) PCT Filed: Dec. 15, 2010

(86) PCT No.: PCT/EP2010/007683
§ 371 (c)(1),
(2), (4) Date: Jun. 4, 2012

(87) PCT Pub. No.: WO2011/072858
PCT Pub. Date: Jun. 23, 2011

(65) Prior Publication Data
US 2013/0164243 A1    Jun. 27, 2013

(30) Foreign Application Priority Data

Dec. 18, 2009    (EP) ..................... 09015681

(51) Int. Cl.
| | |
|---|---|
| A61K 8/898 | (2006.01) |
| A61Q 5/06 | (2006.01) |
| A61Q 5/00 | (2006.01) |
| A61Q 5/10 | (2006.01) |
| A61K 35/36 | (2006.01) |
| A61K 8/37 | (2006.01) |
| A61K 8/42 | (2006.01) |
| A61Q 5/12 | (2006.01) |

(52) U.S. Cl.
CPC ................ *A61K 8/898* (2013.01); *A61Q 5/065* (2013.01); *A61Q 5/004* (2013.01); *A61Q 5/10* (2013.01); *A61K 35/36* (2013.01); *A61K 8/37* (2013.01); *A61K 8/42* (2013.01); *A61Q 5/12* (2013.01)

(58) Field of Classification Search
CPC .......... A61Q 5/12; A61K 35/36; A61K 8/898
See application file for complete search history.

(56) References Cited

U.S. PATENT DOCUMENTS

| 2005/0063934 A1* | 3/2005 | Baker et al. ............... 424/70.122 |
| 2012/0024309 A1* | 2/2012 | Pratt et al. ..................... 132/208 |

FOREIGN PATENT DOCUMENTS

| WO | 2008/152595 A2 | 12/2008 |
| WO | 2009/059455 A1 | 5/2009 |

OTHER PUBLICATIONS

Johnson et al, New Silicone Technologies for Ethnic Hair Care, Dow Corning Corporation, 2003, pp. 1-5.*
International Search Report mailed Jun. 15, 2011.

* cited by examiner

*Primary Examiner* — Paul Dickinson
(74) *Attorney, Agent, or Firm* — Norris McLaughlin & Marcus PA

(57) ABSTRACT

Present invention is related to a conditioning composition for hair comprising at least one cationic and/or cationizable surfactant of amido amine type, at least one aminated silicone and at least one fatty acid lower alcohol ester.

12 Claims, No Drawings

CONDITIONING COMPOSITION FOR HAIR

This application is a 371 application of PCT/EP2010/007683 filed Dec. 15, 2010, which claims foreign priority benefit under 35 U.S.C. §119 of European Application No. 09015681.1 filed Dec. 18, 2009.

The present invention is related to a conditioning composition for hair comprising at least one cationic surfactant, at least one aminated silicone and at least one fatty acid lower alcohol ester.

Conditioning compositions for hair have been known for ages. Various types of conditioners are available on the market and new ones are being introduced almost every day. Although the extremely developed conditioner market, there is still need for improvements.

It is known that consumers with damaged hair are often not satisfied with hair conditioning effect of known conditioners. In case they choose a rich conditioner, the hair afterwards looses its volume and/or body and after a lighter conditioner, hair is not conditioned enough so that it is not combable, does not appear shiny and it is not manageable, etc. In other words, for consumers with damaged hair which is not homogeneous in degree of damage, it is very hard to find a correct conditioner.

On the other hand, fine hair has to be correctly conditioned for improving combability and shine, but this often results in loss of volume and partly body because of, especially damaged fine hair, heavy conditioning ingredients load onto hair. This is certainly not satisfying for consumers.

Therefore, there is a great need for improved conditioner compositions which homogeneously conditions damaged and healthy hair, especially damaged and natural fine hair and does not result in loss of volume and body without changing combing shine and other properties of hair negatively.

It has surprisingly been found out that a composition comprising at least one cationic surfactant of amido amine type, at least one aminated silicone and at least one fatty acid lower alcohol ester conditions damaged and healthy hair excellently homogeneously so that hair becomes combable, has excellent grip, shine, elasticity, volume, body and manageable. Hair fibres consisting of parts with various damage levels in its length are conditioned excellently homogeneously.

Accordingly, the first object of the present invention is a conditioning composition for hair comprising at least one cationic and/or cationizable surfactant of amido amine type, at least one aminated silicone and at least one fatty acid lower alcohol ester.

Further object of the present invention is the use of the composition of the present invention for conditioning hair, especially fine hair, and especially to keep or improve combability, shine, volume, body, elasticity and manageability of hair.

Still further object of the present invention is the method of conditioning hair wherein hair is treated with a composition of the present invention and optionally rinsed off from hair after a processing time of 1 to 30 min.

Compositions of the present invention are suitable for either rinse off or leave in applications. Further object of the present invention is process for conditioning hair wherein a composition according to present invention is applied onto hair and not rinsed off.

Compositions of the present invention comprise at least one cationic and/or cationizable surfactant of amido amine type. Preferably the surfactant is selected from compounds according to the general structure $$R_1\text{-A-}R_2\text{—B}$$

wherein $R_1$ is a saturated or unsaturated, straight or branched alkyl group with 7 to 23 C atoms, $R_2$ is a straight or branched alkyl group with 1 to 4 C atoms, A is a group

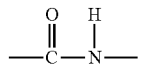

and B is selected from

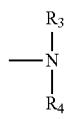

wherein $R_3$ and $R_4$ are the same or different is H or an alkyl with 1 to 4 C atoms, hydroxyl alkyl with 1 to 4 C atoms and di hydroxyl alkyl with 2 to 4 C atoms,

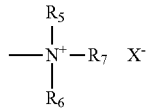

$R_5$, and $R_6$ are the same or different, an alkyl with 1 to 4 C atoms, hydroxyl alkyl with 1 to 4 C atoms and di hydroxyl alkyl with 2 to 4 C atoms, $R_7$ is an alkyl with 1 to 4 C atoms, hydroxyl alkyl with 1 to 4 C atoms or di hydroxyl alkyl with 2 to 4 C atoms and

wherein $R_1$, A and $R_2$ have the above meaning and X is chloride, bromide, methosulfate, Non-limiting suitable examples are palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl methylamine, stearamidopropyl diethylamine, stearamidopropyl dibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, dicocoylethylhydroxyethylmonium methosulfate, cetyltrimethyl ammonium chloride, steartrimonium chloride, behentrimonium chloride, myristyltrimethyl ammonium chloride, distearyldimethyl ammonium chloride, and dibehenyldimethyl ammonium chloride.

Concentration of at least one cationic and/or cationizable surfactant of amido amine type according to the above general structure is in the range of 0.01 to 20%, preferably 0.02 to 15%, more preferably 0.05 to 10% and most preferably 0.1 to 7.5% and in particular 0.25 to 5% by weight calculated to total composition. It should be noted that conditioning compositions can comprise two or more cationic surfactants of amido amine type and above given concentration ranges refer to the total concentration and not individual surfactants.

Composition of the present invention comprises at least one aminated silicone. Aminated silicones are preferably selected from amodimethicones and their derivatives. Suitable non-limiting examples and preferred ones are with their CTFA and/or INCI adopted names amodimethicone, aminopropyl dimethicone, amiopropyl phenyl trimethicone, bis aminopropyl dimethicone, bis aminopropyl/ethoxy aminopropyl dimethicone, PEG-7 amodimethicone, PEG-8 amodimethicone, PG amodimethicone, Trideceth-9 PG amodimethicone and trimethylsiloxyamodimethicone. More preferred are amiopropyl phenyl trimethicone, bis aminopropyl dimethicone, bis aminopropyl/ethoxy aminopropyl dimethicone, diphenyl dimethicone and the most preferred is amiopropyl phenyl trimethicone.

Concentration of at least one aminated silicone compound is in the range of 0.01 to 10%, preferably 0.02 to 7.5%, more preferably 0.05 to 5% and most preferably 0.1 to 5% by weight calculated to total composition. It should be noted that conditioning compositions can comprise two or more aminated silicones and above given concentration ranges refer to the total concentration and not individual surfactants.

Compositions of the present invention comprise at least one fatty acid lower alcohol ester, preferably according to general structure

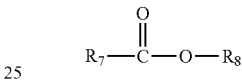

wherein $R_7$ is branched or straight, saturate or unsaturated alkyl group with a chain length of 7 to 23 C atoms which may further comprise one or more additional substitutions on the alkyl chain, and $R_8$ is a branched or straight lower alkyl chain with 1 to 4 C atoms which may comprise one or more substituent such as hydroxyl groups.

Preferred compounds are according to the above general structure wherein $R_7$ is branched or straight, saturate or unsaturated alkyl group with a chain length of 11 to 17 C atoms which may further comprise one or more additional substitutions on the alkyl chain, and $R_8$ is a branched or straight lower alkyl chain with 1 to 4 C atoms which may comprise one or more substitutions such as hydroxyl groups.

Suitable examples are isopropyl laurate, isopropyl myristate, isopropyl palmitate, isopropyl behenate, isopropyl sterate, isopropyl oleate, isopropyl linoleate, isopropyl isostearate, isopropyl arachidate, isobutyl myristate, isobutyl laurate, isobutyl palmitate, isobutyl sterate, isobutyl oleate, isobutyl linoleate, isobutyl behenate, ethyl laurate, ethyl myristate, ethyl palmitate, ethyl stearate, ethyl oleate, ethyl behenate, ethyl oleate, ethyl linoleate, ethyl ricinoleate, butyl laurate, butyl myristate, butyl palmitate, butyl stearate, butyl oleate, butyl behenate, butyl oleate, butyl linoleate and butyl ricinoleate. Preferred are isopropyl laurate, isopropyl myristate, isopropyl palmitate, isopropyl behenate, isopropyl sterate, isopropyl oleate, isopropyl linoleate, isopropyl isostearate and isopropyl arachidate. More preferred are isopropyl laurate, isopropyl myristate, isopropyl palmitate, isopropyl stearate and isopropyl isostearate. Most preferred are isopropyl myristate and/or isopropyl palmitate and/or isopropyl stearate.

Concentration of at least one fatty acid lower alcohol ester is in the range of 0.01 to 10%, preferably 0.02 to 7.5%, more preferably 0.05 to 5% and most preferably 0.1 to 5% by weight calculated to total composition. It should be noted that conditioning compositions can comprise two or more fatty acid lower alcohol ester and above given concentration ranges refer to the total concentration and not individual compounds.

Compositions of the present invention comprise additionally at least one cationic quaternary ammonium surfactant according to the general structure

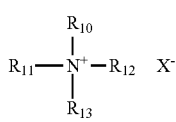

where $R_{10}$ is a saturated or unsaturated, branched or straight alkyl chain with 8-24 C atoms and $R_{11}$ is unsaturated or saturated, branched or straight alkyl chain with 1-24 C atoms and $R_{12}$ and $R_{13}$ are lower alkyl chain with 1 to 4 carbon atoms, wherein all alkyl groups given herein may be substituted with one or more substituent(s), for example hydroxyl groups, and X is anion such as chloride, bromide, methosulfate.

Suitable non-limiting ones are cetrimonium chloride, steartrimonium chloride, cetrimonium bromide, behentrimonium chloride and bromide, dicetyl dimonium chloride, distearyldimethyl ammonium chloride and dibehenyldimethyl ammonium chloride.

Concentration of at least one cationic quaternary ammonium surfactant is in the range of 0.01 to 20%, preferably 0.02 to 15%, more preferably 0.05 to 10% and most preferably 0.1 to 7.5% and in particular 0.25 to 5% by weight calculated to total composition. It should be noted that conditioning compositions can comprise two or more cationic surfactants and above given concentration ranges refer to the total concentration and not individual surfactants.

Thickening agents may be added into the compositions of the present invention. Suitable non-limiting examples are cellulose derivatives such as hydroxylcellulose, methyl cellulose, hydroxymethlyl cellulose, hydroxypropyl cellulose, xanthan gum, guar gum and its derivatives especially non-ionic ones as thickener, which should not principally exclude to use cationic ones as thickener and conditioner, such hydroxypropyl guar, acrylates as the synthetic ones which may be alone or in combination with others available from various suppliers known as polyacrylate-1 crosspolymer with its INCI name and their derivatives. It should be noted that some of the cationic polymers mentioned below as a conditioning agent may also act as a thickener such as Polyquaternium-37 and some of the cationic cellulose and guar derivatives. Thickeners may be included at a concentration of 0.05 to 2.5% by weight calculated to total composition. Concentration of thickener is very much dependent on the thickener its self and also the preparation such as pH value of the composition etc.

In one of the preferred from of the present invention, conditioning compositions comprise at least one cationic polymer as conditioning agent. Suitable cationic polymers are those of best known with their INCI category name Polyquaternium. Typical examples of those are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87 as well as silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21.

It has further been found out that especially those of cationic cellulose type polymers known as Polymer JR type from Amerchol such as Polyquaternium 10 or cationic galactomannans such as cationic guar gum known with trade name Jaguar from Rhône-Poulenc which are chemically for example Guar hydroxypropyl trimonium chloride and cationic tara gum an its derivatives known with INCI name *Caesalpinia spinosa* hydroxypropyltrimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, cationic *Caesalpinia spinosa* gum derivatives, polyquaternium 6, polyquaternium 7, polyquaternium 67 and polyquaternium 70.

The cationic polymers also include the quaternized products of graft polymers from organopolysiloxanes and polyethyl oxazolines described in EP-A 524 612 and EP-A 640 643.

Concentration of at least one cationic polymer is in the range of 0.01 to 5%, preferably 0.01 to 3% more preferably 0.02 to 2.5% and most preferably 0.05 to 2% by weight calculated to total composition.

Compositions of the present invention can be in emulsion form. Emulsion type of conditioning compositions comprise preferably additionally at least one fatty alcohol of the following formula

$R_{20}$—OH where $R_{20}$ is a saturated or unsaturated, branched or non-branched fatty alkyl chain with 8-24 C atoms. Concentration of fatty alcohols is usually less than 20%, preferably less than 15% by weight calculated to total composition. Typical examples to the most useful fatty alcohols are myristyl alcohol, palmityl alcohol, cetyl alcohol, stearyl alcohol, behenyl alcohol and their mixtures. As a mixed fatty alcohol the mostly used one is the cetearyl alcohol as well preferred in the compositions of the present invention.

Oil and/or oily substances are selected from such as silicone oils, either volatile or non-volatile, natural and synthetic oils, fatty alcohol ethers (dialkyl ethers) and fatty acid fatty alcohol esters. Among silicone oils those can be added to the compositions include dimethicone, dimethiconol, polydimethylsiloxane, DC fluid ranges from Dow Corning, arylated silicones such as phenyl methicone, phenyl trimethicone, diphenyl dimethicone, diphenylsiloxy phenyl trimethicone, tetramethyl tetraphenyl trisiloxane, triphenyl trimethicone, and trimethyl pentaphenyl trisiloxane, aminated silicones such as amodimethicone, aqueous emulsion of divinyldimethicone/dimethicone copolymer, preferably with a viscosity of higher than $1\times10^8$ mm$^2$/s, more preferably higher than $1.1\times10^8$ mm$^2$/s, and most preferably higher than $1.2\times10^8$ mm$^2$/s measured at 0.01 Hz and at approximately 25° C.

Concentration of one or more silicone oils is in the range of 0.01 to 5%, preferably 0.01 to 3% more preferably 0.02 to 2.5% and most preferably 0.05 to 2% by weight calculated to total composition.

Natural and/or synthetic oils are comprised in the compositions of the present invention at a concentration in the range of 0.01 to 5%, preferably 0.01 to 3% more preferably 0.02 to 2.5% and most preferably 0.05 to 2% by weight calculated to total composition. Suitable non-limiting examples are such as olive oil, almond oil, avocado oil, wheatgerm oil, ricinus oil and synthetic oils, such as mineral oil.

Fatty acid C6 to C18 fatty alcohol esters as oily substances are comprised in the compositions of the present invention at a concentration in the range of 0.01 to 5%, preferably 0.01 to 3% more preferably 0.02 to 2.5% and most preferably 0.05 to 2% by weight calculated to total composition. Suitable non-limiting examples are such as isopropyl myristate, palmitate, stearate and isostearate, oleyl oleate, isocetyl stearate, hexyl laurate, dibutyl adipate, dioctyl adipate, myristyl myristate and oleyl erucate.

Fatty alcohol ethers (dialkyl ethers) are comprised in the compositions of the present invention at a concentration in the range of 0.01 to 5%, preferably 0.01 to 3% more preferably 0.02 to 2.5% and most preferably 0.05 to 2% by weight calculated to total composition. Suitable non-limiting examples are such as dimyristyl ether, dicetyl ether and dicaprylyl ether.

Conditioning agent is also at least one polyol such as panthenol, glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

$R_8CO(OCH_2CH_2)_nOH$ or

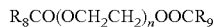
$R_8CO(OCH_2CH_2)_nOOCR_9$ where $R_8$ and $R_9$ are independent from each other saturated, unsaturated or branched or non-branched alkyl chain with 7 to 21 C atoms and n is typically 2-100.

The compositions according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Composition of the present invention may further comprise at least one polyphenol or mixture of polyhenols. Polyphenols are included into compositions of the present invention from a natural plant extract. In principal any natural plant extract rich of polyphenols is suitable within the meaning of the present invention. Within the meaning of the present invention the extracts are liquid extracts and prepared by mixing plant parts such as leaves, fruits, blossoms and roots with a solvent such as water, alcohol, propyleneglycol or mixture of more than one solvent and incubating for certain period of time and filtrating the undissolved plant parts. Suitable aqueous (e.g. steam-distilled) alcoholic or hydro-alcoholic plant extracts known per se are in particular aloe, pineapple, artichoke, arnica, avocado, valerian, bamboo, henbane, birch, stinging nettle, *echinacea*, ivy, wild *angelica*, gentian, ferns, pine needles, silver weed, ginseng, broom, oat, rose hip, *hamamelis*, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, the various "Extrapon®" products, "Herbasol®", "Sedaplant®" and "Hexaplant®".

Extracts and the preparation thereof are also described in "Hagers Handbuch der pharmazeutischen Praxis", 4$^{th}$ Ed. Preferred plant extracts are prepared from *Vitis vinifera, Malus domestica, Camelia sinensis, Juglans regia Ribes Uva-Crispa, Ribes nigrum, Ribes rubrum* and *Punica granatum*. The above mentioned extracts may also be available in the powder form and such are also suitable within the meaning of the present invention.

The polyphenol comprising extracts are included into the compositions of the present invention at a concentration of 0.001 to 10%, preferably 0.005 to 7.5%, more preferably 0.01 to 5% and most preferably 0.05 to 2.5% by weight, calculated to total composition based on dry matter of the extract.

Further in preferred embodiment of the present invention, compositions comprise at least one UV filter and at least one ubichinone of the following formula

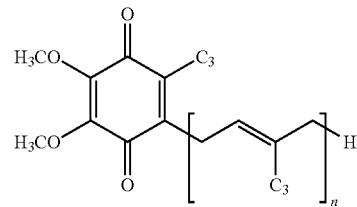

where n is a number between 1 and 10. It should be noted that the compositions of the present invention can certainly comprise more than one ubichinone. Preferred ubichinones are the ones where n is a number between 6 and 10 and especially preferred is Ubichinone 50 where n is 10, also known as Coenzyme Q10. Concentration ubichinone of the above formula in the compositions is from 0.0001 to 1%, preferably from 0.0002 to 0.75%, more preferably from 0.0002 to 0.5% and most preferably from 0.0005 to 0.5% by weight, calculated to total composition.

Compositions of the present invention preferably comprise at least one UV filter. Principally any substance known as UV filter is suitable for the compositions of the present invention. Non-limiting examples are 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof, 3-(4'-methyl benzylidene)-DL-campher, and/or polysilicone-15. Above mentioned UV filters are those oil and water soluble ones for the purpose of protecting hair colour. In other words, anionic and nonionic, oily, UV filters are suitably used in the compositions of the present invention. In the preferred from of the invention the compositions comprise at least one water soluble UV filter and at least one oil soluble one. Further preferred that both UV filters are present at a weight ratio in the range of oil soluble to water soluble UV filter 1:10 to 10:1, preferably 1:5 to 5:1, more preferably 1:3 to 3:1 and most preferably 1:1 in the compositions of the present invention.

The amount of the UV-absorber as a total ranges typically from about 0.01% to 5%, preferably 0.05 to 3%, more preferably from 0.05% to 2.5% and most preferably from 0.1% to 2% by weight, calculated to the total composition.

In another preferred form of the invention, conditioning composition can comprise one or more organic solvent such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylenecarbonate, propyleneglycol, poypropyleneglycols, ethyleneglycol monoethylether, ethylene glycol monobutyl ether, ethylene glycol monophenyl ether, 1-phenylethylalcohol, 2-phenylethylalcohol, o-methoxyphenol. The most preferred ones are ethanol, isopropanol, benzylalcohol and polypropylene glycols. Concentration of organic solvents should not exceed 50% by weight, preferably in the range of 0.1 to 40%, more preferably 0.1 to 30% by weight and most preferably 0.1 to 20% by weight calculated to total composition. It should be noted that concentration of at least one organic solvent is very much dependent on the type of preparation i.e. a solution can contain higher concentration of organic solvent than an emulsion composition.

Conditioning composition of the present invention may comprise at least one glyceryl ether of the following formula

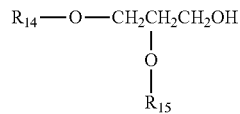

wherein $R_{14}$ is straight or branched, saturated or unsaturated alkyl chain with 4 to 24 C atoms, preferably 4 to 18 and more preferably 4 to 12 C atoms and $R_{15}$ is H, or straight or branched, saturated or unsaturated alkyl chain with 4 to 24 C atoms, preferably 4 to 18 and more preferably 4 to 12 C atoms and most preferably $R_5$ is H, at a concentration of 0.1 to 10%, preferably 0.1 to 5% and more preferably 0.25 to 3% and most preferably 0.5 to 2.5% by weight calculated to total composition.

Suitable unlimited examples are glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether, glyceryl lauryl ether, glyceryl myristyl ether, glyceryl palmityl ether, glyceryl stearyl ether and glyceryl behenyl ether and their mixtures. Most preferred are glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether are glyceryl lauryl ether, and their mixtures.

It should be noted that within the disclosure of the present description, gylceryl decyl ether is used as synonym of decyl glycerine. For the other compounds in the above paragraph the same is valid.

Further in preferred embodiment of the present invention, compositions comprise at least one direct dye. Suitable direct dyes are of cationic, anionic and neutral nitro dyes. It should be noted that they can also be used in combination with each other. In other words a composition according to present invention can comprise an anionic and a cationic dye as well as an anionic and a nitro dye or a cationic and a nitro dye. Certainly the combination of all three dyestuffs is also possible.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of one or more direct dyes in total is in the range of 0.001 to 5% by weight, preferably 0.01 to 4% more preferably 0.05 to 3% and most preferably 0.1 to 2.5% by weight calculated to total composition.

Conditioning compositions of the present invention can comprise at least one surfactant selected from anionic, nonionic and amphoteric surfactants, preferably at a concentration range of 0.5 to 20%, preferably 1 to 15% and more preferably 1 to 10% by weight, calculated to the total composition. At least one surfactant is added into the composition of the present invention as solubilizer and/or emulsifier. The most preferred surfactant is nonionic surfactants.

Among suitable examples, suited are alkyl polyglucosides of the general formula

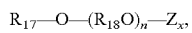

$$R_{17}\text{—}O\text{—}(R_{18}O)_n\text{—}Z_x,$$

wherein $R_{17}$ is an alkyl group with 8 to 18 carbon atoms, $R_{18}$ is an ethylene or propylene group, Z is a saccharide group with 5 to 6 carbon atoms, n is a number from 0 to 10 and x is a number between 1 and 5.

Further nonionic surfactant components are, for example, long-chain fatty acid mono- and dialkanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further nonionic surfactants useful in the compositions of the present invention are $C_{10}$-$C_{22}$-fatty alcohol ethoxylates at a concentration of 0.5 to 10%, preferably 0.5 to 5% by weight, calculated to total composition. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

Conditioning compositions of the present invention can be in the form of emulsions, solutions, gels and dispersions. In the case that solutions and/or gels forms are preferred the appearance can be either with a transparent or opaque. As a product form, foam is as well suited when packed into a pressurized can or delivered through a pump-foamer (non-aerosol). In the case that an aerosol foam preparation is preferred, propellant gas must be added to the formulation. The suitable propellant gasses are carbondioxide, dimethylether and alkanes such as butane, propane, isobutane or their mixtures.

Conditioning compositions of the present invention can comprise additionally any compound customarily found in conditioning compositions such as chelating agents, preservatives and fragrance.

The sequestering agents are selected from polycarboxy acids. The preferred one is ethylene diamine tetraacetic acid, EDTA. Typical useful concentration range for sequestering agents is of 0.01-2.5% by weight calculated to the total composition.

The pH of the compositions according to the present invention is suitably between 2 and 8 and preferably in the range of 2.5 to 6.5, more preferably 3 to 5.5 and most preferably 3.5 to 5.

In principal pH of the compositions can be adjusted with any organic and/or inorganic acids or their mixture. Some of them to mention are phosphoric acid, hydrochloric acid as the inorganic ones and to the organic acids the well known citric acid and lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. It has further been observed that improved conditioning and brightening performance was observed when compositions comprise at the same time at least one hydroxycarboxylic and/or dicarboxylic acids.

Viscosity of the conditioning composition may be adjusted according to the application form and generally should not be more than 100,000 mPa·s at 20° C. measured with Brookfield Rheometer at a shear rate of 10 $\sec^{-1}$.

The following examples are to illustrate the invention, but not to limit. The compositions according to the invention are prepared by mixing the individual components, whereby it is also possible to use pre-mixtures of various ingredients.

EXAMPLE 1

|  | % by weight |
| --- | --- |
| Stearamidopropyldimethylamine | 1.5 |
| Aminopropyl phenyl trimethicone | 0.7 |
| Isopropylpalmitate | 0.2 |
| Hydroxyethyl cellulose | 0.5 |
| Citric acid | q.s. pH 4.0 |
| Fragrance, preservative | q.s. |
| Water | to 100 |

Above composition was used as a leave in composition and applied onto towel dried hair after shampooing and not rinsed off after application. The composition improves combability, shine, elasticity, volume and body and manageability of damaged hair. In addition it was observed that the same properties of hair which included highly damaged tips and relatively healthy root area were improved as well.

EXAMPLE 2

|  | % by weight |
| --- | --- |
| Behenamidopropyldimethylamine | 1 |
| Aminopropyl phenyl trimethicone | 0.5 |
| Cetearyl alcohol | 7 |
| Ceteareth-20 | 3 |
| Isopropylmyristate | 0.5 |
| Lactic acid | q.s. pH 4.0 |
| Fragrance, preservative | q.s. |
| Water | to 100 |

The composition improves combability, shine, volume and body of damaged hair both leave in and rinse off usage.

EXAMPLE 3

|  | % by weight |
| --- | --- |
| Stearamidopropyldimethylamine | 0.5 |
| Aminopropyl phenyl trimethicone | 0.5 |
| Isopropyl myristate | 0.5 |

-continued

| | % by weight |
|---|---|
| Cetearyl alcohol | 7 |
| Cetrimonium chloride | 1.5 |
| Citric acid | q.s. pH 4.0 |
| Fragrance, preservative | q.s. |
| Water | to 100 |

The composition conditions inhomogeneously damaged hair homogeneously so that hair is combable, has shine, elasticity, volume and it is manageable.

EXAMPLE 4

| | % by weight |
|---|---|
| Stearamidopropyldimethylamine | 1.0 |
| Aminopropyl phenyl trimethicone | 0.3 |
| Isopropyl myristate | 0.5 |
| Dicocoylethylhydroxyethylmonium methosulfate | 0.5 |
| Behenyl alcohol | 5 |
| Ceteareth-20 | 2 |
| Polyquaternium-10 | 0.2 |
| Dimethicone | 0.5 |
| Lactic acid | q.s. pH 4.2 |
| Fragrance, preservative | q.s. |
| Water | to 100 |

EXAMPLE 5

| | % by weight |
|---|---|
| Behenamidopropyldimethylamine | 0.75 |
| Polyquaternium-6 | 0.1 |
| Amodimethicone | 0.5 |
| Panthenol | 0.5 |
| Isopropylmyristate | 0.2 |
| Cetearyl alcohol | 5.0 |
| Ceteareth-20 | 1.5 |
| Lactic acid | q.s. pH 5.0 |
| Fragrance, preservative | q.s. |
| Water | to 100 |

The above composition was used as a rinse off conditioner after cleansing hair. In dry state it was observed that hair was easily combable, had elasticity, volume and body.

EXAMPLE 6

| | % by weight |
|---|---|
| Behenamidopropyldimethylamine | 0.75 |
| Isopropylmyristate | 0.2 |
| Aminopropyl phenyl trimethicone | 0.3 |
| Cetearyl alcohol | 5.0 |
| Ceteareth-20 | 1.5 |
| Basic red 51 | 0.1 |
| Basic orange 31 | 0.05 |
| Basic yellow 87 | 0.01 |
| Basic blue 99 | 0.01 |
| Lactic acid | q.s. pH 4.0 |
| Fragrance, preservative | q.s. |
| Water | to 100 |

The above composition provided intensive red shine to the hair.

EXAMPLE 7

| | % by weight |
|---|---|
| Behenamidopropyldimethylamine | 0.75 |
| Isopropylmyristate | 0.2 |
| Aminopropyl phenyl trimethicone | 0.3 |
| Cetearyl alcohol | 7 |
| Ceteareth-20 | 3 |
| Dicetyl ether | 0.2 |
| Benzophenone-3 | 0.4 |
| Panthenol | 0.5 |
| Phenyl trimethicone | 0.3 |
| Citric acid | q.s. pH 4.0 |
| Fragrance, preservative | q.s. |
| Water | to 100 |

The above composition was especially suitable for coloured and/or highlighted hair. The coloured hair treated with the above conditioner is exceptionally shiny, well combable and has elasticity, volume and body.

EXAMPLE 8

| | % by weight |
|---|---|
| Behenamidopropyldimethylamine | 0.75 |
| Isopropylmyristate | 0.2 |
| Aminopropyl phenyl trimethicone | 0.3 |
| Cetearyl alcohol | 7 |
| Cetrimonium chloride | 1.2 |
| Benzophenone-3 | 0.4 |
| Polyquaternium-10 | 0.5 |
| Phenyl trimethicone | 0.2 |
| Citric acid | q.s. pH 4.0 |
| Fragrance, preservative | q.s. |
| Water | to 100 |

The above composition was especially suitable for coloured and/or highlighted hair. The coloured hair treated with the above conditioner is exceptionally shiny, well combable and has elasticity, volume and body.

EXAMPLE 9

| | % by weight |
|---|---|
| Behenamidopropyldimethylamine | 0.75 |
| Isopropylmyristate | 0.2 |
| Aminopropyl phenyl trimethicone | 0.3 |
| DC HMW 2220 | 0.2 |
| Cetearyl alcohol | 7 |
| Ceteareth-20 | 3 |
| Benzophenone-4 | 0.2 |
| Glycerin | 3 |
| Guar hydroxyproly trimonium chloride | 0.3 |
| Basic red 51 | 0.1 |
| Citric acid | q.s. pH 4.2 |
| Fragrance, preservative | q.s. |
| Water | to 100 |

Above conditioner gives dark blonde hair red shimmer.

EXAMPLE 10

| | % by weight |
|---|---|
| Behenamidopropyldimethylamine | 0.75 |
| Isopropylmyristate | 0.2 |
| Aminopropyl phenyl trimethicone | 0.3 |
| Cetearyl alcohol | 7 |
| Ceteareth-20 | 3 |
| Octylmethoxy cinnamate | 0.4 |
| Glycerin | 3 |
| Trimethyl pentaphenyl trisiloxane | 0.3 |
| Basic red 51 | 0.01 |
| Basic yellow 87 | 0.1 |
| Basic orange 31 | 0.02 |
| Citric acid | q.s. pH 4.2 |
| Fragrance, preservative | q.s. |
| Water | to 100 |

Above conditioner gives light blonde hair additional blond shine.

EXAMPLE 11

| | % by weight |
|---|---|
| Behenamidopropyldimethylamine | 0.75 |
| Isopropylmyristate | 0.2 |
| Aminopropyl phenyl trimethicone | 0.3 |
| Cetearyl alcohol | 7 |
| Ceteareth-20 | 3 |
| Octylmethoxy cinnamate | 0.4 |
| Glycerin | 3 |
| Phenyl trimethicone | 0.3 |
| Coenzyme Q10 | 0.08 |
| *Vitis vinifera* (dry matter) | 0.1 |
| Citric acid | q.s. pH 4.2 |
| Fragrance, preservative | q.s. |
| Water | to 100 |

Above conditioner enhances combability, shine, volume body and elasticity. Hair treated with the above conditioner is excellently manageable and easily styled.

EXAMPLE 12

| | % by weight |
|---|---|
| Behenamidopropyldimethylamine | 0.75 |
| Isopropylmyristate | 0.2 |
| Aminopropyl phenyl trimethicone | 0.3 |
| Polyquaternium-6 | 0.2 |
| Cetearyl alcohol | 7 |
| Steartrimonium chloride | 1 |
| Glycerin | 3 |
| Carnosine | 0.6 |
| Dimethicone | 0.3 |
| Coenzyme Q10 | 0.08 |
| Isopropyl myristate | 0.2 |
| Lactic acid | q.s. pH 3.8 |
| Fragrance, preservative | q.s. |
| Water | to 100 |

Above conditioner enhances combability, shine, volume body and elasticity. Hair treated with the above conditioner is excellently manageable and easily styled. Above conditioner was also used as leave in conditioner and bodyfying effects was especially enhanced.

EXAMPLE 13

| | % by weight |
|---|---|
| Behenamidopropyldimethylamine | 0.75 |
| Isopropylmyristate | 0.2 |
| Aminopropyl phenyl trimethicone | 0.3 |
| Cocamidoproyl betaine | 0.8 |
| Steartrimonium chloride | 1 |
| Glycerin | 3 |
| Coenzyme Q10 | 0.08 |
| Isopropyl myristate | 0.1 |
| Lactic acid | q.s. pH 3.8 |
| Fragrance, preservative | q.s. |
| Water | to 100 |

Above composition had a viscosity below 500 mPa·s and was filled into a pump foamer and used as leave in conditioner on a freshly washed and towel dried hair. Hair was excellently shiny and bodified also excellently combable.

The above composition was also used as aerosol foam and therefore filled into an aerosol can with 10% propane-butane mixture as a propellant. The above results were confirmed.

The above composition can also be used as a pump spray.

EXAMPLE 14

| | % by weight |
|---|---|
| Cetylstearylalcohol | 5.0 |
| Behenamidopropyldimethylamine | 0.75 |
| Isopropylmyristate | 0.2 |
| Aminopropyl phenyl trimethicone | 0.3 |
| Ceteareth 20 | 1.0 |
| Panthenol | 0.4 |
| Hydroxypropyl Guar Hydroxypropyltrimonium Chloride | 0.3 |
| Ethylhexyl glycerin | 0.8 |
| Tetramethyl tetraphenyl trisiloxane | 0.2 |
| *Ribes nigrum* (dry matter) | 0.1 |
| Avocado extract | 0.5 |
| Fragrance, preservative | q.s. |
| Malic acid | q.s. to pH 3.5 |
| Wasser | ad 100.0 |

EXAMPLE 15

| | % by weight |
|---|---|
| Cetylstearylalcohol | 5.0 |
| Stearyltrimethylammoniumchlorid | 1.0 |
| Isopropylstearate | 0.2 |
| Aminopropyl phenyl trimethicone | 0.3 |
| Stearamidopropyldimethyl amine | 1.0 |
| Benzylalcohol | 2.5 |
| Trimethyl pentaphenyl trisiloxane | 0.3 |
| Ethylhexyl glycerin | 0.9 |
| Fragrance, preservative | q.s. |
| Lactic acid | q.s. pH 3.5 |
| Wasser | ad 100.0 |

Above composition is applied onto shampooed hair and processed for 5 min and rinsed off from hair. It was observed that wet hair is easily combable. In the dry state combability, manageability, elasticity and shine were very much improved. Furthermore, into the above conditioner composition, hair direct dye Basic red 51 was included at a concentration of 0.15% by weight. After use on dark blonde hair an excellent red shine was observed on the hair.

EXAMPLE 16

Foam conditioner

|  | % by weight |
| --- | --- |
| Quaternium-80 | 0.2 |
| Polyquaternium-11 | 0.7 |
| PEG-60-hydrogenated *ricinus* oil | 0.5 |
| Behenamidopropyldimethylamine | 0.75 |
| Isopropylmyristate | 0.2 |
| Aminopropyl phenyl trimethicone | 0.3 |
| Ubichinone | 0.075 |
| Benzophenone-3 | 0.3 |
| Fragrance, preservative | q.s. |
| Lactic acid | q.s. to pH 3.1 |
| Wasser | ad 100.0 | pH of the composition is adjusted to 3.4. The composition is suitable for leave-in and rinse off. In leave-in application, amount used is obviously less than in the case of a rinse of application. The composition is packed into an aerosol can with 90/10 ratio, by weight, liquid composition to propellant. As propellant propane, butane mixture is used.

Into the above composition 0.1%, by weight, Acid red 52 was added. It was possible to realize red shimmer onto dark blonde hair.

The invention claimed is:

1. Conditioning composition for hair comprising:
   at least one cationic and/or cationizable surfactant of amido amine type;
   at least one aminated silicone selected from the group consisting of aminopropyl dimethicone, aminopropyl phenyl trimethicone, bis aminopropyl dimethicone, bis aminopropyl/ethoxy aminopropyl dimethicone, PEG-7 amodimethicone, PEG-8 amodimethicone, PG amodimethicone, Trideceth-9 PG amodimethicone and trimethylsiloxyamodimethicone; and
   at least one fatty acid lower alcohol ester selected from the group consisting of isopropyl laurate, isopropyl myristate, isopropyl palmitate, isopropyl behenate, isopropyl stearate, isopropyl oleate, isopropyl linoleate, isopropyl isostearate, isopropyl arachidate, isobutyl myristate, isobutyl laurate, isobutyl palmitate, isobutyl sterate, isobutyl oleate, isobutyl linoleate, isobutyl behenate, ethyl laurate, ethyl myristate, ethyl palmitate, ethyl stearate, ethyl oleate, ethyl behenate, ethyl oleate, ethyl linoleate, ethyl ricinoleate, butyl laurate, butyl myristate, butyl palmitate, butyl stearate, butyl oleate, butyl behenate, butyl oleate, butyl linoleate and butyl ricinoleate.

2. Composition according to claim 1 wherein at least one cationic and/or cationizable surfactant of amido amine type is selected from compounds according to the general structure

wherein $R_1$ is a saturated or unsaturated, straight or branched alkyl group with 7 to 23 C atoms, $R_2$ is a straight or branched alkyl group with 1 to 4 C atoms, A is a group

and B is selected from

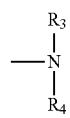

wherein $R_3$ and $R_4$ are the same or different is H or an alkyl with 1 to 4 C atoms, hydroxyl alkyl with 1 to 4 C atoms and di hydroxyl alkyl with 2 to 4 C atoms,

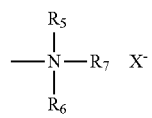

$R_5$, and $R_6$ are the same or different, an alkyl with 1 to 4 C atoms, hydroxyl alkyl with 1 to 4 C atoms and di hydroxyl alkyl with 2 to 4 C atoms, $R_7$ is an alkyl with 1 to 4 C atoms, hydroxyl alkyl with 1 to 4 C atoms or di hydroxyl alkyl with 2 to 4 C atoms and

wherein $R_1$, A and $R_2$ have the above meaning and X is chloride, bromide and methosulfate.

3. Composition according to claim 1, wherein at least one aminated silicone is aminopropyl phenyl trimethicone.

4. Composition according to claim 1, wherein at least one fatty acid lower alcohol ester is isopropyl myristate and/or isopropyl palmitate and/or isopropyl stearate.

5. Composition according to claim 1, comprising at least one cationic quaternary ammonium surfactant according to the general structure

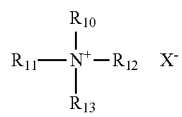

where $R_{10}$ is a saturated or unsaturated, branched or straight alkyl chain with 8-24 C atoms and $R_{11}$ is unsaturated or saturated, branched or straight alkyl chain with 1-24 C atoms and $R_{12}$ and $R_{13}$ are lower alkyl chain with 1 to 4 carbon atoms, wherein all alkyl groups given herein may be substituted with one or more substituent(s), for example hydroxyl groups, and X is anion such as chloride, bromide, methosulfate.

6. Composition according to claim 1, comprising at least one thickening agent.

7. Composition according to claim 1, comprising at least one cationic polymer.

8. Composition according to claim 5 comprising at least one fatty alcohol of the following formula

where $R_{20}$ is a saturated or unsaturated, branched or non-branched fatty alkyl chain with 8-24 C atoms and at least one nonionic surfactant as an emulsifier.

9. Composition according to claim 1, comprising at least one direct dye.

10. Composition according claim 1, comprising one or more of compounds selected from protein hyrolyzates, polyphenols, ubichinones of the general structure

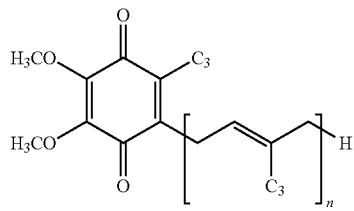

where n is a number between 1 and 10, UV filter, organic solvent and chelating agent.

11. Composition according to claim 1 having a pH in the range of 2.0 to 8.0.

12. Process for conditioning hair wherein a composition according to claim 1 is applied onto wet or dry hair and optionally rinsed off from hair.

* * * * *